(12) United States Patent
Yagita

(10) Patent No.: US 6,818,624 B2
(45) Date of Patent: Nov. 16, 2004

(54) THERAPEUTIC AGENT FOR A CANCER AND METHOD OF SCREENING THE SAME, AND HEALTH-CARE AUXILLARY FOOD

(75) Inventor: Akikuni Yagita, Tokyo (JP)

(73) Assignee: Orient Cancer Therapy Co., Ltd., Tokyo (JP)

( * ) Notice: Subject to any disclaimer, the term of this patent is extended or adjusted under 35 U.S.C. 154(b) by 56 days.

(21) Appl. No.: 10/189,209

(22) Filed: Jul. 3, 2002

(65) Prior Publication Data

US 2003/0064076 A1 Apr. 3, 2003

Related U.S. Application Data

(62) Division of application No. 09/748,726, filed on Dec. 26, 2000, now Pat. No. 6,464,981.

(30) Foreign Application Priority Data

Jun. 16, 2000 (JP) ........................................ 2000-182124

(51) Int. Cl.$^7$ ...................... A61K 31/704; A61K 35/84; A01N 63/00; C12Q 1/00; C12N 1/00
(52) U.S. Cl. ................... 514/26; 424/93.5; 424/195.15; 435/4; 435/253.4; 435/254.1; 514/54; 514/59; 514/777; 514/885
(58) Field of Search ...................... 435/4, 253.4, 254.1; 514/54, 59, 777, 885, 26; 424/93.5, 195.15

(56) References Cited

U.S. PATENT DOCUMENTS

| | | | |
|---|---|---|---|
| 5,053,398 A | 10/1991 | Mori et al. | ..................... 514/54 |
| 5,641,761 A | 6/1997 | Takahashi et al. | ............. 514/54 |
| 6,238,660 B1 | 5/2001 | Yagita | ..................... 424/93.44 |
| 2003/0153514 A1 * | 8/2003 | Yagita | ......................... 514/26 |

FOREIGN PATENT DOCUMENTS

| | | |
|---|---|---|
| JP | 06-080574 | 3/1994 |
| JP | 07309713 A | 11/1995 |
| JP | 10-139670 | 5/1998 |
| JP | 11-071297 | 3/1999 |
| JP | 11-292786 | 10/1999 |

OTHER PUBLICATIONS

Yamamoto et al., "Immunopotentiating Activity of the Water–soluble Lignin Rich Fraction Prepared from LEM— The Extract of the Solid Culture Medium of Lentinus edodes Mycelia" *Biosci, Biotech, Biochem.*, 61 (11), pp 1909–1912, 1997.

Morinaga et al., "An in vivo Study of Hepatic and Splenic Interleukin–1β mRNA Expression Following Oral PSK or LEM Administration" *Jpn. J. Cancer Res.* 85, pp 1298–1303, Dec. 1994.

Kano et al., "Augmentation of the antitumor effect of adoptive immunotherapy by in vivo sensitization of EL–4 lymphoma and pre–treatment with sizofiran" *Biotherapy*, 11, pp 1–6, 1998.

M. Ghoneum. NK Immunomodulation by active Hemicellulose Compound in 17 Cancer Patients. 1994. Natural Immunity, 13(4) p. 228.

Singleton et al., 1991. Dictionary of Microbiology and Molecular Biology, John Wiley and sons, p., 460.

* cited by examiner

*Primary Examiner*—Ralph Gitomer
*Assistant Examiner*—Kailash C. Srivastava

(74) *Attorney, Agent, or Firm*—Kilyk & Bowersoy, P.L.L.C.

(57) ABSTRACT

A therapeutic agent for a cancer comprising a therapeutically effective amount of an active ingredient, wherein the therapeutic agent is used referring to an ability of acting on NK cell antigen receptor NKR-P1 of NKT cell as an index of the ability to activate the NKT cell.

2 Claims, 7 Drawing Sheets

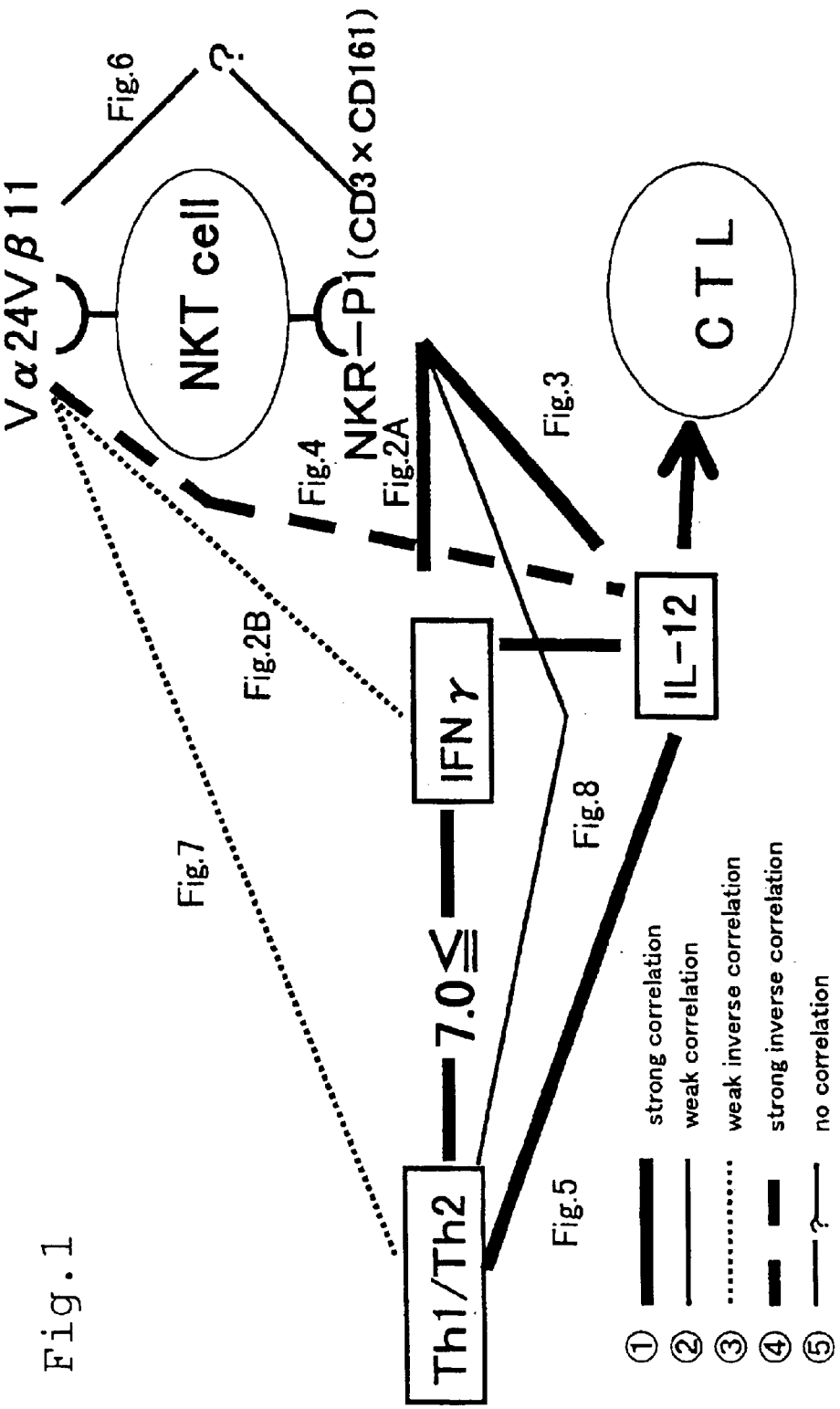

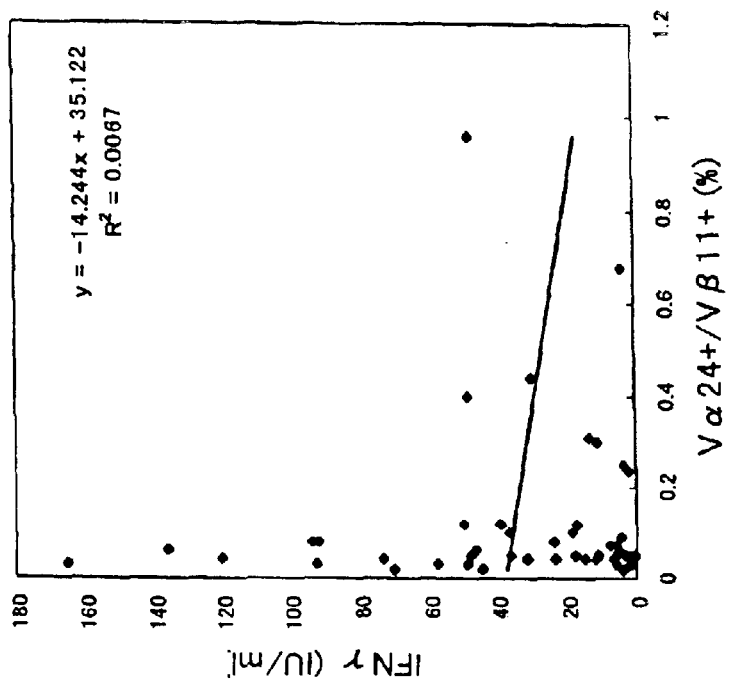
Fig. 2B  All cases n=37
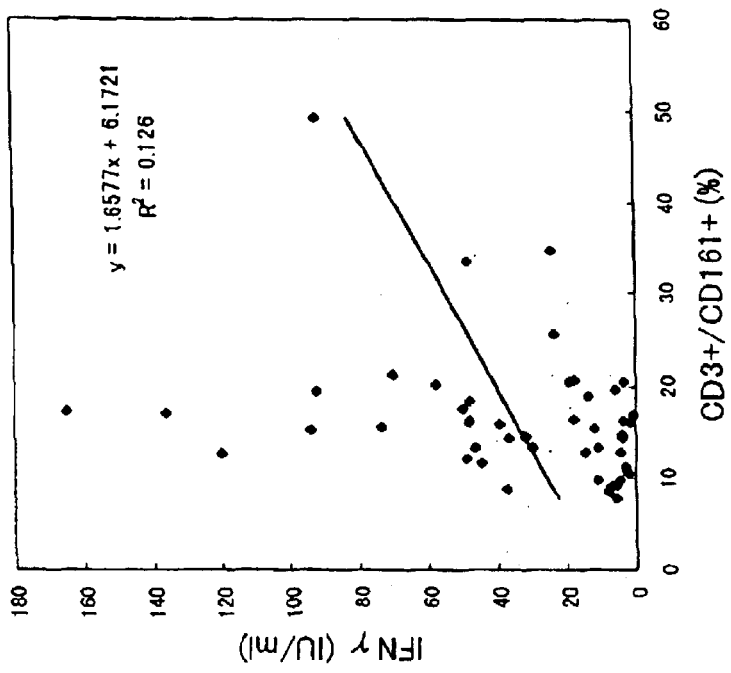
Fig. 2A  All cases n=37

Fig. 4
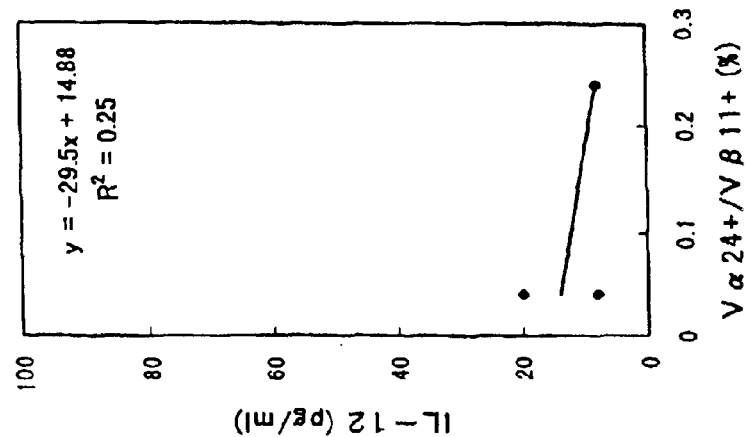
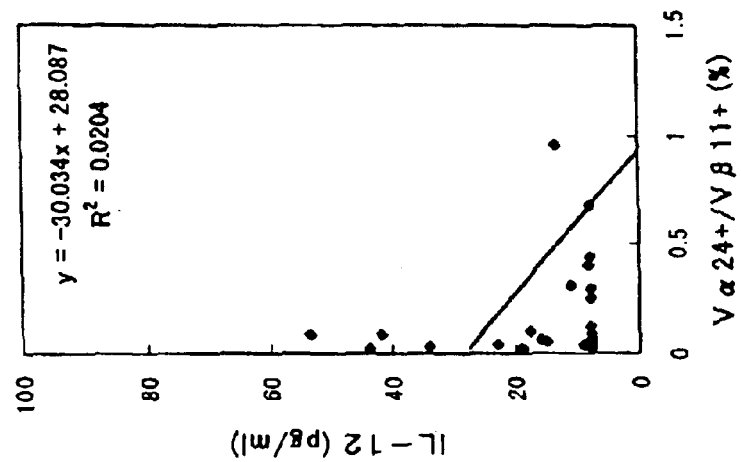
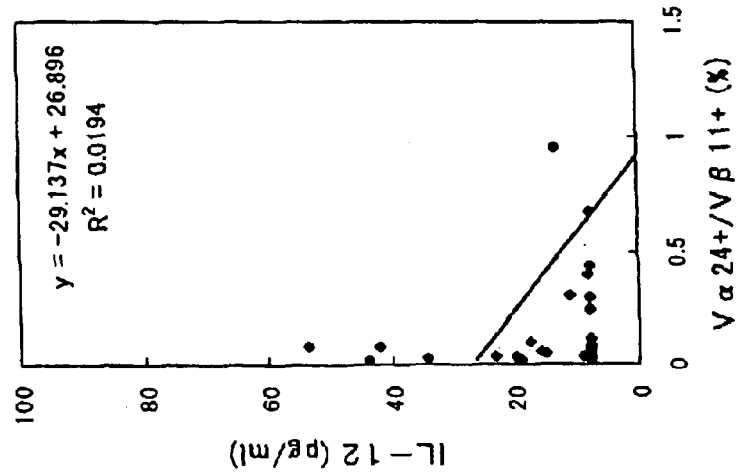

Fig. 7
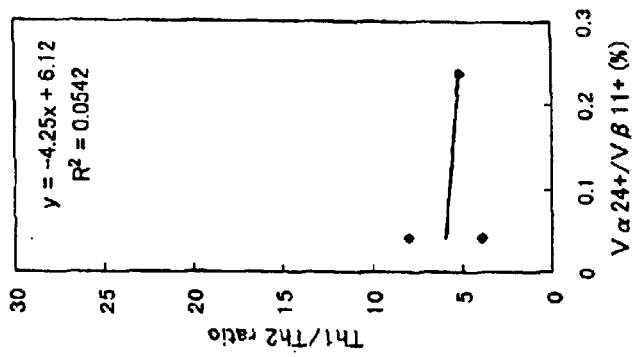
All cases n=37
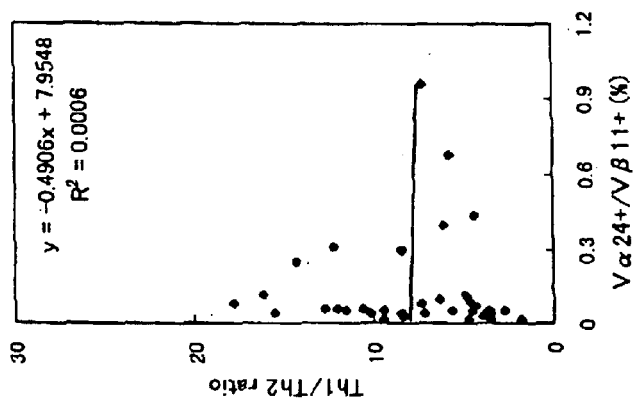
CR, PR, NC n=34
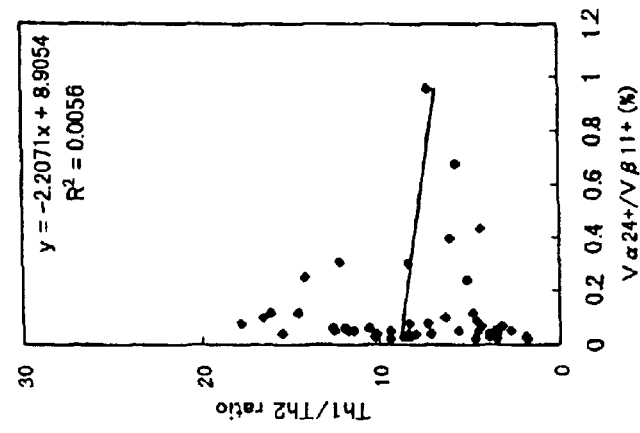
PD n=3

THERAPEUTIC AGENT FOR A CANCER AND METHOD OF SCREENING THE SAME, AND HEALTH-CARE AUXILLARY FOOD

This is a continuation application of U.S. patent application Ser. No. 09/748,726 which was filed on Dec. 26, 2000 now U.S. Pat. No. 6,464,981.

BACKGROUND OF THE INVENTION

1. Field of Invention

The present invention relates to a therapeutic agent for cancers intended to activate natural killer T (NKT) cells, to a method of screening such a therapeutic agent and to health-care auxiliary food preparations for oral uptake which are taken up with view to obtaining anti-cancer activity intended to activate NKT cells.

2. Description of the Related Art

Screening of substances useful for the prevention or therapy of cancers has been made laying importance on their direct action onto cancer cells. It has been known that immune activators are useful in the therapy of cancers. However, the compounds obtained as immune activators are all weak in their anti-cancer effect and no sufficient therapeutic effect against cancers has been achieved yet by immune therapy alone or even by immune therapy in combination with chemical therapy.

Dr. Yagita, the inventor or the present invention, paid attention to the usefulness of substances that induce interleukin 12 (IL-12) in vivo and found that AHCC, a processed product of the mycelia of Lentinus edodes (Berk.) Sing. (also called shiitake), has such a function as above and established a method of treating cancers, i.e., a new immunological therapeutic method. IL-12 itself is known to have an anti-cancer effect but cause side effects when administered directly to patients and the patients tend to be intolerable to the therapy. Therefore, IL-12 itself could hardly be used as an anti-cancer agent. However, the preparation containing AHCC which Dr. Yagita reported has achieved remarkable curing and life lengthening effects in the therapy of cancers. In other words, Dr. Yagita has achieved an object of treating cancers by administration of an effective amount for inducing IL-12 in vivo of AHCC (JP 10-139670A).

IL-12 has an activity of increasing production of interferon γ (IFN-γ), an activity of activating and enhancing natural killer (NK) cells, lymphokine activated killer (LAK) cells, and killer T cells, which are competent for cell mediated immunity. INF-γ is a cytokine that induces an immune response of an organism in a state where T helper 1 (Th1) is active. In this state, NKT cells or killer T cells readily exhibit their effects and in other words production of interleukin 2 (IL-2) and IL-12 occurs on a large scale. Killer T cells and LAK cells are known to be cells that participate in cancer immunity. NK cells are also reported to participate in anti-cancer activity of an organism. In the case of NK cells, Dr. Yagita proved that the clinical anti-cancer effect and their activity do not correlate with each other and the amount of induced production of IL-12 and NK activity show a complete inverse correlation therebetween. Therefore, it is concluded that no NK cell participates in anti-cancer activity in humans.

Currently, Dr. Yagita has indicated that a substance that has activity of inducing the production of IL-12 is likely to be a promising carcinostatic substance.

However, in some patients who suffer cancers, the administration of AHCC does not sufficiently induce the production of IL-12 to give no therapeutic effect or even when it induces the production of IL-12, it gives no sufficient therapeutic effect. Accordingly, there has been a keen demand for the development of a novel therapeutic agent for cancers which agent acts in a mechanism other than the anti-cancer effect which AHCC has.

It has been known that in the mechanism of cancer immunity, the amount of cytokine produced or induced in vivo is an important factor and hence a therapeutic method has been proposed and practiced which administers, induces or cause to be produced a cytokine that is believed to have anti-cancer activity to treat the cancer. However, although the relationships between cancers and immunity or between cancers and cytokines have been made clearer, the effect of curing the cancers and of life lengthening have been observed in 50% or less of patients who suffer the cancers. Furthermore, recently, natural killer T (NKT) cells have been found as cells that participate in cancer immunity (Cui J. et al., Science 278, 1623, 1997). The NKT cell is one of various types of cells that participate in the immune system and has, for example, potent cytokine productivity, in particular IFN-γ productivity, and a function of cytotoxicity through Fas or perforin. Therefore, it is anticipated that activation of the cells will further increase curing or life lengthening effects in those patients who suffer cancers.

Taniguchi et al., have found a specific glycolipid antigen. This antigen is recognized by specific T cell antigen receptor (TCR), Vα24Vβ11, that NKT cells have. Taniguchi et al. reported that the antigen is an α-galactosylceramide. Furthermore, Taniguchi et al. proved that in cancer-carrying mice administered with α-galactosylceramide, NKT cells are activated and metastasis of the cancer is suppressed though the elimination of cancer is not observed.

It has been reported that NKT cells contain NK cell antigen receptor (hereinafter, sometimes referred to also NKR-P10; natural killer receptor P1) as another receptor (Special issue: Basis and Clinic of NKT Cells; Saishin Igaku (CurrentMedicine), Vol. 55, No. 4, 2000, p. 818–823). NKR-P1 also participates in the activation of NKT cells.

SUMMARY OF THE INVENTION

An object of the present invention is to elucidate the mechanism of activating NKT cells and provide a novel and useful therapeutic agent for cancers having an ability of activating NKT cells.

With view to solving the above problems, the present inventor has made extensive research on cancer immunity cascade for the prevention or therapy of cancers and as a result he has found that in the cascade in which activated NKT cells competent for cancer immunity participate, two different antigen receptors, i.e., NKR-P1 and Vα24Vβ11 have quite different activities from each other. The present invention has been achieved based on this discovery.

That is, the present invention provides the followings:

(1) A therapeutic agent for a cancer comprising a therapeutically effective amount of an active ingredient, wherein the therapeutic agent is used referring to an ability of acting on natural killer receptor P1 of natural killer T cell as an index of the ability to activate the natural killer T cell.

(2) The therapeutic agent for a cancer as described in (1) above, wherein the active ingredient comprises a substance having a capability of selectively acting on natural killer receptor P1 of natural killer T cell to activate the natural killer T cell.

(3) The therapeutic agent for a cancer as described in (2) above, wherein the active ingredient comprises at least one substance selected from products derived from the mycelia of fungi having an ability of selectively acting on natural killer receptor P1 of natural killer T cell to activate the natural killer T cell.

(4) The therapeutic agent for a cancer as described in (2) above, wherein the substance in the active ingredient comprises at least one selected from polysaccharides derived from the filtrate of culture of the mycelium of Shizophyllum commune Fries, processed products of the mycelium of Coriolus versicolor (Fr.) Quel., and processed product of the mycelium of Shiitake.

(5) The therapeutic agent for a cancer as described in (4) above, wherein the substance in the active ingredient comprises a sugar component having α-1,3-glucoside linkage structure.

(6) The therapeutic agent for a cancer as described in (1) above, wherein the agent comprises a processed product of the mycelium of *Shizophyllum commune* Fries or a polysaccharide derived from the filtrate of a culture of the mycelium of *Shizophyllum commune* Fries, a processed product of the mycelium of Shiitake, and a processed product of the mycelium of *Ganoderma lucidum* (Fr.) Karst.

(7) The therapeutic agent for a cancer as described in (1) above, wherein the agent comprises 20 to 60% by weight of a processed product of the mycelium of *Shizophyllum commune* Fries or a polysaccharide derived from the filtrate of a culture of the mycelium of *Shizophyllum commune* Fries, 20 to 60% by weight of a processed product of the mycelium of Shiitake, and 5 to 40% by weight of a processedproduct of the mycelium of *Ganoderma lucidum* (Fr.) Karst.

(8) The therapeutic agent for a cancer as described in (1) above, wherein the agent comprises 30 to 50% by weight of a processed product of the mycelium of *Shizophyllum commune* Fries or a polysaccharide derived from the filtrate of a culture of the mycelium of *Shizophyllum commune* Fries, 30 to 50% by weight of a processed product of the mycelium of Shiitake, and 10 to 0.30% by weight of a processed product of the mycelium of *Ganoderma lucidum* (Fr.) Karst.

(9) The therapeutic agent for a cancer as described in (1) above, wherein the agent is in the form of a formulation suitable for oral administration.

(10) The therapeutic agent for a cancer as described in (1) above, wherein the therapeutic agent selectively acts on natural killer receptor P1.

(11) The therapeutic agent for a cancer as described in (1) above, wherein the therapeutic agent induces mass production of interferon γ as a result of selective action on natural killer receptor P1 and shifts the ratio of T helper 1 cell/T helper 2 cell, Th1/Th2, toward a value at which an immune system where mainly Th1 acts operates.

(12) The therapeutic agent for a cancer as described in (1) above, wherein natural killer receptor P1 is determined by measuring CD3 and CD161, cell surface markers, and the ability of activating natural killer T cell.

(13) A method for screening therapeutic agents for a cancer, comprising screening a therapeutic agent for a cancer based on an ability of acting on natural killer receptor P1 of natural killer T cell as an index of the ability to activate the natural killer T cell.

(14) The therapeutic agent for a cancer as described in (1) above, wherein it is used as a health-care auxiliary food preparation for oral uptake.

(15) A method of treating a cancer, comprising administering to a patient suffering a cancer a therapeutically effective amount of an active ingredient, said agent being used referring to an ability of acting on natural killer receptor P1 of natural killer T cell as an index of the ability to activate the natural killer T cell.

(16) A health-care auxiliary food comprising a substance having a capability of selectively acting on natural killer receptor P1 of natural killer T cell to activate the natural killer T cell.

(17) A commercial medium carrying information as described in (1) above.

(18) A commercial method utilizing information as described in (1) above.

BRIEF DESCRIPTION OF THE DRAWINGS

FIG. 1 is a diagram illustrating an overview of the correlation among various cytokines.

FIG. 2A is a diagram illustrating the correlation of CD3×CD161 with the amount of interferon γ (IFN-γ) (IU/ml).

FIG. 2B is a diagram illustrating the correlation of Vα24Vβ11 with the amount of IFN-γ (IU/ml)

FIG. 4 is a diagram illustrating the correlation of IL-12 (pg/ml) with Vα24Vβ11.

FIG. 7 is a diagram illustrating the correlation of Vα24Vβ11 with Th1/Th2 ratio.

DETAILED DESCRIPTION OF THE INVENTION

Figure 3:
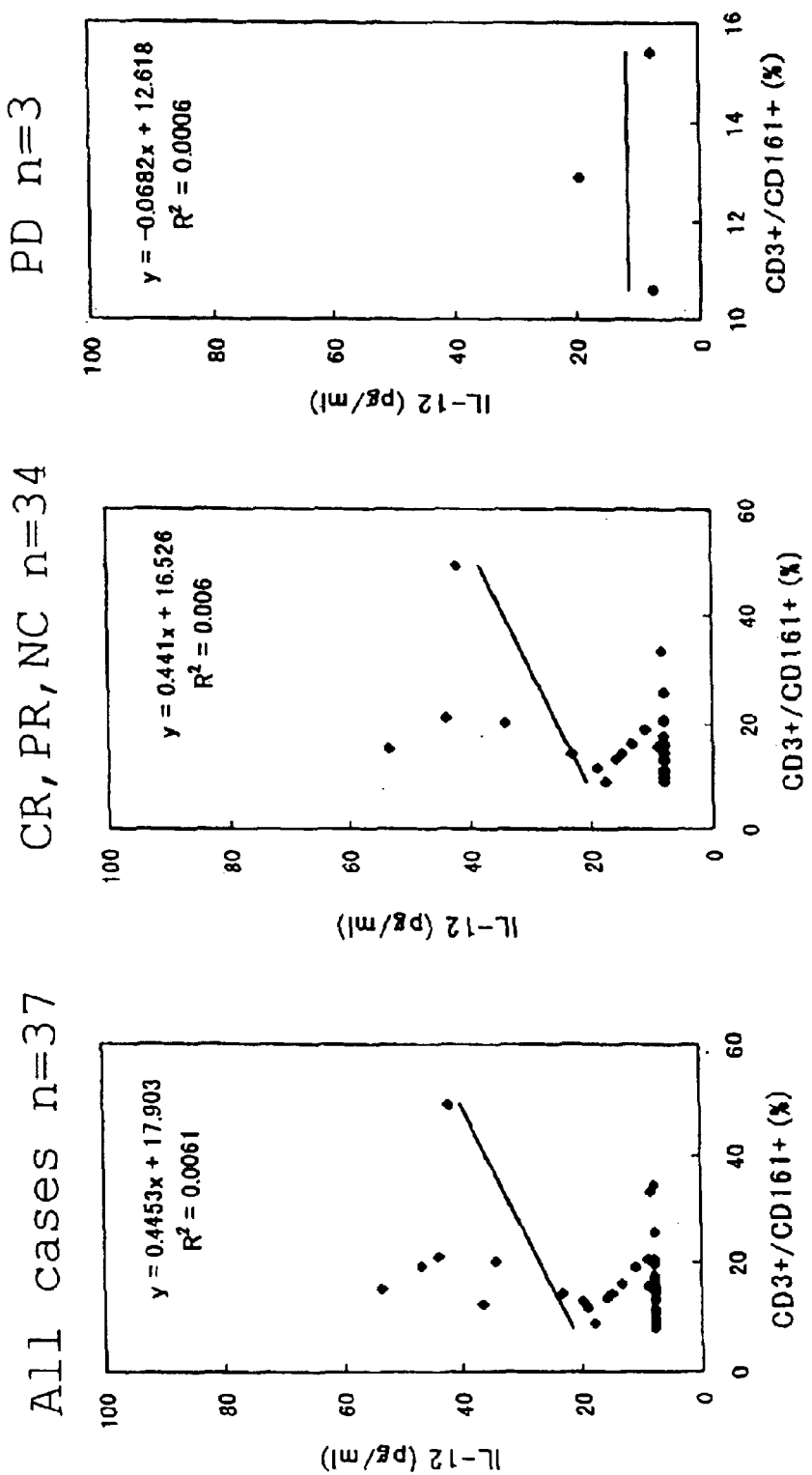
FIG. 3 is a diagram illustrating the correlation of IL-12 (pg/ml) with CD3×CD161.

Hereinafter, the present invention will be described in detail.

The present invention has been practiced by studying the correlation of the clinical effect with cytokines. The present inventor has administered mycelia-derived products to 37 patients suffering cancer diseases and determined the levels of various cytokines (Table 1). The results are shown in FIGS. 2 to 8 as data illustrating the correlation to obtain a diagram for illustrating the correlation of various cytokines as illustrated in Table 1.

As shown in FIG. 1, it has been proved that there are strong positive correlations between Th1/Th2 ratio and IL-12, Th1/Th2 ratio and IFN-γ, IFN-γ and IL-12, IL-12 and the ratio of CD3×CD161 (NKR-P1) -positive cells (CD3+/CD161+), and IFN-γ and the ratio of CD3×CD161 (NKR-P1)-positive cells, respectively and that there is a strong inverse correlation between IL-12 and Vα24Vβ11-positive cells (TCR Vα24+/TCR Vβ11+).

Accordingly, in the present invention, it has been demonstrated that NKT cells in which Vα24Vβ11 T cell antigen receptors are stimulated show a strong inverse correlation with IL-12 and weak inverse correlation with IFN-γ production amount and Th1/Th2 ratio and that the stimulation by NKT cell to Vα24Vβ11 serves to inhibit the immune function. It has been presumed that the stimulation to Vα24Vβ11 could lead to mass production of interleukin 4 (IL-4), which causes immune suppression. On the other hand, it has been demonstrated that when an NK cell antigen receptor, NKR-P1, in NKT cell is stimulated, the NKT cell shows strong positive correlation with IL-12 and IFN-γ but a weak positive correlation with Th1/Th2 ratio and that the stimulation to NKR-P1 results in the activation of immune function.

As a result, upon screening substances for the ability of activating NKT cells, it is necessary to perform screening utilizing as an index at least the action to NKR-P1. Moreover, screening must be performed utilizing as an index the fact that in the activation of NKT cells, the action is selective to NKR-P1, which is NK cell antigen receptor. In addition, it is important that the action should not affect Vα24Vβ11. As a result of selective action of the substance thus screened, mass production of IFN-γ is induced and in immune responses, the immune system can be shifted toward the direction where Th1 operates. Use of such a selected substance can provide a therapeutic agent for a cancer which is very useful for immune therapy for cancers. In the selection of such a useful substance, the ability of activation of a substance when it is administered in an organism can be assayed by determining its stimulation, if any, of cells carrying NKR-P1, i.e., cells having CD3× CD161, which are cell surface markers. The screened therapeutic agent may be an oral health-care auxiliary food preparation for oral uptake which comprises, for example, components derived from fungal mycelia.

The therapeutic agent for a cancer of the present invention comprises a therapeutically effective amount of a substance having an ability of selectively acting on NKR-P1 of an NKT cell to activate the NKT cell and preferably is administered orally.

The therapeutic agent for a cancer of the present invention is a health-care auxiliary food preparation which is orally taken in order to obtain anti-cancer effects.

The therapeutic agent for a cancer is effective in the therapy of lung cancer, pulmonary adenomatosis, thymoma, thyroid cancer, bladder cancer, colon cancer, rectal cancer, cecum cancer, ureteral cancer, breast cancer, cervical cancer, brain cancer, lingual cancer, pharynx cancer, nasal cancer, larynx cancer, gastric cancer, hepatic cancer, biliary tract cancer, testicular cancer, ovarian cancer, uterine cancer, malignant melanoma, liposarcoma, esophagus cancer, pancreatic cancer, prostatic cancer, etc. However, the present invention is not limited to these cancers.

The therapeutic agent for a cancer of the present invention comprises at least one substance selected from fungal mycelia processed products as an active ingredient. More specifically, products derived from the mycelium of Scizophyllum commune Fries, such as SPG (sizofiran: Kaken Seiyaku Co., Ltd.), i.e., a polysaccharide obtained from filtrate of the culture of mycelium of Schizophyllum commune Fries and SCP (oral uptake preparation of processed product of the mycelium of Shizophyllum commune Fries (Tozai Iyaku Kenkyusho, Ltd.)), processed product of the mycelium of Coriolus versicolor (Fr.) Quel. (Kawaratake), such as PSK (Krestin), and processed product of the mycelium of Lentinus edodes (Berk.) Sing., such as AHCC and LEM (Noda Shokkin Kogyo Co., Ltd) are effective. SPG (sizofiran: Kaken Seiyaku Co., Ltd.) is used as a carcinostatic agent for only certain types of cancers (Taito Co., Ltd. and Kaken Seiyaku Co., Ltd.). The same will do as to PSK (Krestin).

In the present invention, using the ability of inducing IL-12 production in an organism and the ability of selectively acting on NKR-P1 of NKT cell to activate the NKT cell as indices, usefulness of processed products of the mycelium of Shizophyllum commune Fries, polysaccharides derived from the filtrate of culture of the mycelium of Shizophyllum commune Fries, processed products of the mycelium of Coriolus versicolor (Fr.) Quel., such as PSK (Krestin), and processed product of the mycelium of Lentinus edodes (Berk.) Sing., such as AHCC and LEM, has been discovered and the present invention has been achieved based thereon. That is, the present invention provides a therapeutic agent for a cancer which comprises a composition containing as an active ingredient at least one selected from polysaccharides derived from the filtrate of culture of the mycelium of Shizophyllum commune Fries, such as SPG, processed products of the mycelium of Coriolus versicolor (Fr.) Quel., such as PSK Lentinus edodes (Berk.) Sing. (Krestin), and processed product of the mycelium of Lentinus edodes (Berk.) Sing., such as AHCC and LEM and which selectively acts on NKR-P1 of NKT cell to activate the NKT cell.

Further, the present inventor has found that products derived from the mycelia of fungi having the ability of selectively acting on the NKR-P1 of NKT cell to activate the NKT cell may be sugar components having α-1,3- and/or α-1,4-glucoside linkage structure, particularly preferably at least α-1,3-glucoside linkage structure. Also, he has found that the substance having the ability of activating NKT cells may be a composition derived from the mycelia of fungi containing polysaccharides and/or 2 to 10 oligosaccharides having this structure. The present inventor has studied products derived from various fungi and the ability of activating NKT and their relation with the components thereof. As a result he has found that the existence of the above sugar structure is essential for the ability of the product derived from the mycelia of fungi to selectively act on NKR-P1 of NKT cells to activate the NKT cells. In addition, he has confirmed that the β-1,3- and β-1,6-glucoside linkage structures of the mycelia have the ability of selectively acting on NKR-P1 of NKT cells to activate the NKT cells.

The dose of the therapeutic agent for a cancer of the present invention comprising a composition containing the mycelia of fungi sufficient for selectively acting on NKR-P1 to activate NKT cells is about 1 to about 2,000 mg/kg body weight/day and administered for 10 days to 12 months, preferably by oral administration. Of course, the therapeutic agent of the present invention may be taken up parenterally by decreasing the dose and preparing the therapeutic agent so as to have a quality bearing parenteral administration.

For the therapeutic agent for a cancer of the present invention that selectively acts on NKR-P1 of NKT cells to activate the NKT cells, the processed products of the mycelia or substances derived from the mycelia of fungi may be used alone or two or more of them may be used in combination simultaneously.

Further, the present invention may be a therapeutic agent for a cancer or a health-care auxiliary food preparation for oral uptake intended to exhibit an anti-cancer effect, comprising a substance having the ability of inducing production of IL-12 and a substance having the ability of selectively acting on NKR-P1 to activate NKT cells.

As an example for such a blend composition, at least two substances selected from processed products of the mycelium of Shizophyllum commune Fries, such as SCP, polysaccharides derived from the filtrate of culture of the mycelium of Shizophyllum commune Fries, such as SPG, processed product of the mycelium of Lentinus edodes (Berk.) Sing., such as AHCC and LEM, and processed products of the mycelium of Ganoderma lucidum (Fr.) Karst., such as MAK (Noda Shokkin Kogyo Co., Ltd.), are blended. Most of these have been used as an immune activator so as to obtain anti-cancer effects. In contrast, the present invention has found the relationship between the combination of these and the ability of inducing IL-12 production and the ability of selectively acting on NKR-P1 of NKT cells to activate the NKT cells and established its superiority over the anti-cancer effect of conventional carcinostatic agents (20% availability).

Preferred combination is a ternary composition comprising a processed product of the mycelium of *Shizophyllum commune* Fries or a polysaccharide derived from the filtrate of a culture of the mycelium of *Shizophyllum commune* Fries, a processed product of the mycelium of *Lentinus edodes* (Berk.) Sing., and a processed product of the mycelium of *Ganoderma lucidum* (Fr.) Karst. More particularly, an optimal combination is a blend composition of 20 to 60% by weight, preferably 30 to 50% by weight of a processed product of the mycelium of *Shizophyllum commune* Fries or a polysaccharide derived from the filtrate of a culture of the mycelium of Shizophyllum commune Fries, 20 to 60% by weight, preferably 30 to 50% by weight of a processed product of the mycelium of *Lentinus edodes* (Berk.) Sing., and 5 to 40% by weight, preferably 10 to 30% by weight of a processed product of the mycelium of *Ganoderma lucidum* (Fr.) Karst. The blend composition is effective as a therapeutic agent for a cancer or a health-care auxiliary food preparation for oral uptake intended to obtain anti-cancer effect.

The amount of oral uptake of the blend composition of the invention is usually about 1 to 2,000 mg/Kg body weight/day for adults. The dosage regimen may be adjusted depending on the amount of induced IL-12 production and/or the degree of selectively acting on NKR-P1 of NKT cells to activate the NKT cells. The period of administration is from 10 days to 12 months.

The polysaccharides obtained from the filtrate of a culture of the mycelium of *Shizophyllum commune* Fries has already been put on the market as SPG (sizofiran) by Kaken Seiyaku Co., Ltd. and Taito Co., Ltd. The method for producing them includes those disclosed in, for example, JP-B-Sho-52-4634 and JP-B-Sho-52-44634.

Processed products of the mycelium of *Lentinus edodes* (Berk.) Sing., such as LEM, and processed products of the mycelium of *Ganoderma lucidum* (Fr.) Karst., such as MAK, have already been put on the market by Noda Shokkin Kogyo Co., Ltd.

They can be produced, for example, by the following method. That is, rice bran is added to bagasse (sugar cane crush residue) and blended well. After adjusting the water content, the mixture is filled in a certain container to form a solid culture medium, which is then subjected to high pressure steam sterilization. Then, a preliminarily cultured mycelium of each fungus is inoculated on the medium and incubated in a culture chamber at 23° C. for 4 months to grow mycelium. The culture medium on which the mycelium has proliferated is crushed and subjected to autolysis treatment. Thereafter, the thus treated culture medium is extracted with warm water for 15 hours in the case of the processed product of the mycelium of *Lentinus edodes* (Berk.) Sing. and the processed product of the mycelium of *Ganoderma lucidum* (Fr.) Karst. The extract is filtered through a membrane filter to remove microorganisms and the filtrate is concentrated and dried to obtain powder (cf. JP-B-Hei-7-1435, JP-A-Hei-1-312980, JP-B-Sho-51-19013, and JP-B-Sho-53-18591).

The processed products of the mycelium of *Shizophyllum commune* Fries are one of the components of the mycelium and are oil-soluble. Therefore, they can be extracted by extraction treatment with a suitable organic solvent, for example, acetone. The extract is filtered to remove microorganisms to obtain a filtrate, which is then concentrated and dried to obtain powder. In the present invention, this oral uptake preparation (SCP (Tozai Iyaku Kenkyusho, Ltd.)) can be used. The processed products of the mycelia of other fungi may be prepared by similar treatments depending of the solubility characteristics (water-soluble or oil-soluble).

The oral uptake preparation may be formulated into tablets, powders, capsules, syrups, etc. The preparation may also be formulated by blending one or more of additives such as conventional excipients, disintegrating agents, binders, and lubricants using conventional means. Further, if needed, one or more of corrigents, colorants, perfumes, stabilizers, antimicrobial agents, and antiseptics may be added.

The therapeutic agent for a cancer of the present invention may be administered in the form of a composition that selectively acts on NKR-P1 of NKT cells to activate the NKT cells, optionally containing an effective amount of a composition that induces production of IL-12 orally or intravenously or intramuscularly, preferably by an oral route that enables continuous self-control by patients themselves.

The health-care auxiliary food preparation for oral uptake of the present invention that comprises a composition that selectively acts on NKR-P1 of NKT cells to activate the NKT cells, optionally containing an effective amount of a composition that induces production of IL-12, is a health-care auxiliary food preparation for oral uptake that is expected to give anti-cancer effects when it is taken up.

As described above, the present invention provides a novel composition that selectively acts on NKR-P1 of NKT cells to activate the NKT cells and makes it clear the relationship between the ability of inducing production of IL-12 and the ability of selectively acting on NKR-P1 of NKT cells to activate the NKT cells and hence a material carrying the information on the above in a commercial medium is very useful. In addition, commercial utilization of the information can provide means for distinguishing the value of the product and commercial methods using the information are very useful.

EXAMPLES

Examples of the present invention will be described below in order to describe the present invention more specifically. However, the present invention should not be limited thereto and various modification may be made without departing from the scope of the present invention.

Example 1

One (1) kg of the composition (IL-X) consisting of 40% by weight of a processed product of the mycelium of *Shizophyllum commune* Fries (SCP: Tozai Iyaku Kenkyusho, Ltd.), 40% by weight of processed product of the mycelium of *Lentinus edodes* (Berk.) Sing. (LEM (registered trademark): Noda Shokkin Kogyo Co., Ltd.), 20% by weight of a processed product of the mycelium of *Ganoderma lucidum* (Fr.) Karst. (MAK: Noda Shokkin Kogyo Co., Ltd.) was uniformly blended and ternary blended granules were prepared by a fluid granulation method using a spraying-drying process. The granules were orally administered to patients in a dose of 6 g/day/body for 3 months. NKT cell and IL-12 were measured before, after 1 month and after 3 months from the onset of the treatment, respectively, in order to confirm the effect of the granules. About 85% of the patients for whom the activation of NKT cells by selective action on NKR-P1 of the NKT cells and induction of production of IL-12 were confirmed showed significant cancer regression effect and about 20% of them showed complete regression of cancer.

Example 2

One (1) kg of the composition (IL-X) consisting of 40% by weight of a processed product of the mycelium of *Shizophyllum commune* Fries (SCP: Tozai Iyaku Kenkyusho, Ltd.), 40% by weight of processed product of the mycelium of *Lentinus edodes* (Berk.) Sing. (LEM (registered trademark): Noda Shokkin Kogyo Co., Ltd.), 20% by weight of a processed product of the mycelium of *Ganoderma lucidum* (Fr.) Karst (so-called Reishi or Mannentake) (MAK: Noda Shokkin Kogyo Co., Ltd.) was uniformly blended and the blended powder was formulated into fine particles by a wet granulation method. The fine particles were filled in hard gelatin capsules in an amount of 3 g/capsule to obtain an encapsulated agent. The encapsulated agent was administered to patients in a dose of 2 capsules/day/body for 3 months. As a result, the usefulness equivalent to that of the granule of Example 1 was confirmed.

Clinical Example 1

The present inventor determined IFN-γ, CD3×CD161, Vα24Vβ11, IL-12, and Th1/Th2 ratio and correlation between the cytokines paying attention to the kinetics of various cytokines in patients suffering cancers (37 cases). The patients were administered with the components of fungal mycelium (polysaccharides) alone or in combination with OK432 (Picibanil: Chugai Seiyaku Co., Ltd.). All the administered fungal mycelium components (polysaccharides) were those having the ability of inducing production of IL-12 and the ability of activating NKT cells. Table 1 shows the levels of respective cytokines after the patients suffering various cancers were administered with various substances derived from various fungi. Table 2 shows the drugs administered to the patients shown in Table 1. The dose was such that 3 to 6 g/day of the drug was orally administered for an administration period shown in Table 1. Of the 37 cases, 6 cases showed complete recovery, 14 cases showed partial recovery, 14 cases showed no response (no progress of cancer: NC), and 3 cases were ineffective (PD).

TABLE 1

| Disease | J | P | TCR · Vα24+/ Vβ11+ (%) | CD3+/ CD161+ (%) | Th1/Th2 (%) | IL-12 (pg/ml) | IFN γ (IU/ml) | IL-10 (pg/ml) |
|---|---|---|---|---|---|---|---|---|
| Left breast cancer, Liver metastasis | CR | 31 | 0.05 | 10.9 | 9.4 | 7.8 | 2.4 | 97 |
| Left breast cancer | CR | 10 | 0.03 | 20.3 | 8.3 | 34.1 | 57.4 | 226 |
| Gastric cancer, Lymphoid metastasis | CR | 12 | 0.04 | 25.7 | 3.5 | 7.8 | 23.4 | 723 |
| Cecum cancer | CR | 24 | 0.06 | 13.5 | 12.0 | 15.6 | 46.3 | 276 |
| Left breast cancer | CR | 6 | 0.31 | 19.1 | 12.2 | 10.9 | 13.5 | 631 |
| Sigmoid colon cancer | CR | 22 | 0.10 | 8.9 | 6.3 | 17.5 | 37.0 | 373 |
| Hypopharynx cancer, Local relapse | PR | 9 | 0.07 | 9.1 | 4.3 | 7.8 | 5.6 | 551 |
| Gastric cancer | PR | 9 | 0.05 | 11.4 | 4.5 | 7.8 | 3.1 | 329 |
| Gastric cancer | PR | 28 | 0.05 | 9.8 | 2.7 | 7.8 | 10.8 | 169 |
| Right breast cancer | PR | 25 | 0.02 | 21.2 | 9.4 | 43.7 | 69.7 | 426 |
| Left breast cancer, Bone metastasis | PR |  | 0.08 | 49.3 | 7.3 | 41.8 | 91.7 | 209 |
| Left breast cancer, Right breast metastasis | PR | 3 | 0.02 | 14.8 | 1.8 | 7.8 | 4.0 | 598 |
| Small bowel sarcoma, Liver metastasis | PR | 5 | 0.00 | 15.6 | 10.2 | 8.9 | 73.3 | 599 |
| Esophagus cancer | PR | 2 | 0.40 | 33.4 | 6.0 | 8.1 | 48.5 | 994 |
| Uterine cancer | PR | 3 | 0.25 | 163.4 | 14.2 | 7.8 | 3.5 | 103 |
| Ovarian cancer | PR | 16 | 0.44 | 13.5 | 4.3 | 7.8 | 30.0 | 246 |
| Prostatic cancer, Multiple bone metastasis | PR | 8 | 0.05 | 16.1 | 11.5 | 7.8 | 47.8 | 383 |
| Rectal cancer | PR | 10 | 0.02 | 20.5 | 3.5 | 7.8 | 3.2 | 410 |
| Hepatic cancer | PR | 3 | 0.08 | 15.3 | 17.8 | 53.5 | 93.6 | 99 |
| Sigmoid colon cancer, Liver metastasis, Bone metastasis | PR | 6 | 0.96 | 16.4 | 7.2 | 13.2 | 47.8 | 284 |
| Right breast cancer, Lung metastasis | NC | 9 | 0.05 | 14.5 | 5.6 | 14.9 | 36.6 | 305 |
| Rectal cancer, Lung metastasis | NC | 7 | 0.68 | 14.5 | 5.7 | 7.8 | 4.0 | 154 |
| Left lung cancer, Right lung metastasis | NC | 16 | 0.06 | 9.8 | 10.6 | 7.8 | 4.6 | 198 |
| Gastric cancer | NC | 5 | 0.04 | 9.1 | 7.1 | 7.8 | 6.9 | 180 |
| Right pulmonary adenocarcinoma | NC | 2 | 0.30 | 13.4 | 8.4 | 7.8 | 10.8 | 211 |
| Sigmoid colon cancer | NC | 25 | 0.02 | 11.8 | 4.7 | 18.8 | 44.5 | 295 |
| Breast cancer, Lung metastasis | NC | 3 | 0.12 | 20.8 | 4.8 | 7.8 | 17.4 | 565 |
| Lung cancer | NC | 3 | 0.03 | 16.2 | 3.9 | 7.8 | 1.5 | 359 |
| Pancreatic cancer | NC | 3 | 0.04 | 14.6 | 15.5 | 23.0 | 31.6 | 320 |

TABLE 1-continued

| Disease | J | P | TCR · Vα24+/ Vβ11+ (%) | CD3+/ CD161+ (%) | Th1/Th2 (%) | IL-12 (pg/ml) | IFN γ (IU/ml) | IL-10 (pg/ml) |
|---|---|---|---|---|---|---|---|---|
| Hepatic cancer | NC | 18 | 0.06 | 17.2 | 12.7 | 236.0 | 136.0 | 253 |
| Right breast cancer | NC | 9 | 0.09 | 13.0 | 4.6 | 7.8 | 4.4 | 443 |
| Gastric cancer | NC | 10 | 0.12 | 17.7 | 16.1 | 7.8 | 49.6 | 338 |
| Squamous cell carcinoma (left lung) | NC | 9 | 0.05 | 16.5 | 3.6 | 7.8 | 17.6 | 519 |
| Gastric cancer, Liver metastasis | NC | 10 | 0.04 | 12.8 | 8.4 | 122.0 | 120.0 | 246 |
| Ovarian cancer | PD | 4 | 0.04 | 15.4 | 8.0 | 7.8 | 11.5 | 115 |
| Uterine cancer | PD | 10 | 0.24 | 10.6 | 5.1 | 7.8 | 2.0 | 401 |
| Prostatic cancer, Multiple bone metastasis | PD | 6 | 0.04 | 12.9 | 3.9 | 19.6 | 14.7 | 961 |

J: Judgment
P: Period of Administration (Month)

TABLE 2

| Disease | Drug Administered (Polysaccharide, Glycolipid) |
|---|---|
| Left breast cancer, Liver metastasis | AHCC, IL-X |
| Left breast cancer | AHCC, IL-X, PSK |
| Gastric cancer, Lymphoid metastasis | AHCC, IL-X |
| Cecum cancer | AHCC, SCP, SPG |
| Left breast cancer | AHCC, PSK |
| Sigmoid colon cancer | AHCC, PSK |
| Hypopharynx cancer, Local relapse | AHCC, IL-X, PSK, SPG, OK432, SCP |
| Gastric cancer | AHCC, IL-X, PSK, SPG, OK432 |
| Gastric cancer | AHCC, PSK |
| Right breast cancer | AHCC, IL-X |
| Left breast cancer, Bone metastasis | IL-X, PSK |
| Left breast cancer Right breast metastasis | AHCC, IL-X, PSK, SPG, OK432, SCP |
| Small bowel sarcoma, Liver metastasis | AHCC, PSK, SPG, OK432 |
| Esophagus cancer | AHCC, PSK |
| Uterine cancer | AHCC, PSK, SCP |
| Ovarian cancer | AHCC, PSK, SPG, OK432 |
| Prostatic cancer, Multiple bone metastasis | AHCC, PSK |
| Rectal cancer | AHCC, PSK |
| Hepatic cancer | AHCC, PSK |
| Sigmoid colon cancer, Liver metastasis, Bone metastasis | AHCC, PSK |
| Right breast cancer, Lung metastasis | AHCC, IL-X, PSK, SPG, OK432, SCP |
| Rectal cancer, Lung metastasis | AHCC, IL-X, PSK, SCP |
| Left lung cancer, Right lung metastasis | AHCC, IL-X, PSK, SPG, OK432, SCP |
| Gastric cancer | AHCC, IL-X, PSK, SPG, OK432, SCP |
| Right pulmonary adenocarcinoma | IL-X, PSK |
| Sigmoid colon cancer | AHCC, IL-X |
| Breast cancer, Lung metastasis | AHCC, IL-X, PSK, SPG, OK432, SCP |
| Lung cancer | AHCC, IL-X, PSK, SPG, OK432, SCP |
| Pancreatic cancer | AHCC, PSK, SPG |
| Hepatic cancer | AHCC, PSK |
| Right breast cancer | AHCC, PSK, SPG, OK432, SCP |
| Gastric cancer | AHCC, PSK |
| Squamous cell carcinoma (left lung) | AHCC, PSK, SPG, OK432 |
| Gastric cancer, Liver metastasis | AHCC, PSK |
| Ovarian cancer | AHCC, IL-X, PSK, SPG, OK432 |
| Uterine cancer | AHCC, PSK, SPG, OK432 |
| Prostatic cancer, Multiple bone metastasis | AHCC, PSK, SPG, OK432 |

Vα24+/Vβ11+ means a Vα24Vβ11 positive cell, that is, a cell that has cell surface markers, Vα24 and Vβ11, on the surface of the cell. CD3+/CD161+means a CD3×CD161 positive cell, that is, a cell that has cell surface markers, CD3 and CD161, on the surface of the cell. In Table 1, CR indicates complete recovery (4 weeks having elapsed after disappearance of the cancer), PR indicates partial recovery (the cancer having reduced by 50% or more), NC indicates no response (the growth of the cancer having been suppressed to 50% or less or proliferation being suppressed to within 25%), and PD indicates ineffectiveness (the growth of cancer being 25% or more).

Methods for measurement of cells and various cytokines will be described below.

Measurement of NKT Cells

Measurement of the activation of NKT cells, particularly the activation due to the action on NKR-P1 can be performed by examining an increase in number of NKT cells by measuring cell surface antigens (CD3 and CD161) that exist specifically on the cell surface of NKT cells. More specifically, for monocytes in peripheral blood, those cells that are CD3 positive and CD161 positive are assayed. That is, CD3 and CD161, cell surface antigens of NKT cells, are determined with monoclonal antibodies by two color tests using flow cytometry. That NKT cells are activated means that the proportion of NKT cells in monocyte is 10% or more. The ability of activating NKT cells means the function of increasing the proportion of NKT cells to 10% or more, or the function of increasing the proportion of NKT cells after the administration of a substance being more than the proportion of NKT cells before the substance is administered.

Using the blood of a patient, cells in the blood were measured by two color test using flow cytometry for the proportion of cells that were positive to CD3 and CD161 by a conventional method. As the antibodies to CD3 and CD161, CD3-PC5 (Coulter) and CD161 (Becton Dickinson) were used.

Of the activation of NKT cells, the activation by the action on Vα24Vβ11 can be performed by examining an increase in number of NKT cells by measuring Vα24 and Vβ11 that exist specifically on the cell surface of NKT cells. More specifically, for monocytes in peripheral blood, those cells that are Vα24 positive and Vβ11 positive are assayed. That is, Vα24 and Vβ11 were determined with monoclonal antibodies (TCR-Vα24PE and TCR-Vβ11FITC; Beckman Coulter) by Two Color tests using flow cytometry.

Preparation of Samples for Measuring Cytokines

First, monocytes were removed from the blood of a patient suffering cancer. Heparin added peripheral blood obtained from the patient was 2-fold diluted with phosphate buffered saline (PBS) and mixed. The mixture was then overlaid on Ficoll-Conray solution (density: 1.077) and centrifuged at 400G for 20 minutes. Then, the monocyte layer was collected. After washing, a 10% fetal bovine serum (FBS) -added RPMI-1460 medium was supplemented to adjust the density of monocyte to $1 \times 10^6$ cells/ml. To 200 μl of the obtained cell suspension was added phytohemagglutinin (hereinafter abbreviated as PHA) (DIFCO) to a concentration of 20 μg/ml and cultivated in the wells of a 96-well microplate at 37° C. for 24 hours in the presence of 5% $CO_2$. This was used as a sample for measuring cytokines in the cultured cell suspension.

Measurement of IL-12

IL-12 was measured by an ELISA method using the kit manufactured by R&D SYSTEMS. Actually, 50 μl of Assay Diluent RD1F, a diluent for measurement, and 200 μl of a standard solution or the sample prepared in Example 1 were dispensed in each well of a 96-well microplate and left to stand at room temperature for 2 hours for reaction. Thereafter, 200 μl of a horse radish peroxidase (hereinafter, abbreviated as HRP) labeled anti-IL-12 antibody was dispensed to each well and left to stand at room temperature for 2 hours. The reaction mixture in each well was removed and the well was washed 3 times. Thereafter, 200 μl of a coloring substrate solution was dispensed and left to stand at room temperature for 20 minutes. Then, 50 μl of an enzyme reaction termination solution was dispensed. The absorbance of each well was measured at 450 nm using 550 nm as a reference using Emax (Wako Pure Chemical Industry Co., Ltd.). The amount of IL-12 was expressed in terms of pg/ml. The ability of inducing production of IL-12 means the function of increasing the amount of IL-12 produced by peripheral blood monocytes upon stimulation by 7.8 pg/ml or more (7.8 pg/ml being the measurement limit), or the function of increasing the amount of IL-12 produced after the administration of a substance being more than the amount of IL-12 before the substance is administered.

Measurement of IFN-γ

IFN-γ was measured by an enzyme immunoassay method (EIA method) using an IFN-γ EASIA kit (BioSource Europe). Actually, 50 μl of a standard solution or the sample prepared as described above diluted to 2-fold was dispensed in each well of a 96-well microplate and 50 μl of HRP-labeled anti-IFN-γ antibody was dispensed and allowed to react at room temperature for 2 hours with shaking. After removing the reaction mixture, each well was washed 3 times. Then, 200 μl/well of a coloring substrate solution was dispensed and allowed to react at room temperature for 15 minutes, followed by dispensing 50 μl/well of an enzyme reaction termination solution. The absorbance of each well was measured at 450 nm and 490 nm using 630 nm as a reference using Emax (Wako Pure Chemical Industry Co., Ltd.) The amount of IL-12 was expressed in terms of IU/ml.

Measurement of IL-10

IL-10 was measured by a solid phase enzyme immunoassay method (ELISA) using an IFN-γ EASIA kit (BioSource Europe). The same procedures as those in the measurement of IFN-γ were followed except that an anti-IL-10 antibody was used instead of the anti-IFN-γ antibody. The amount of IL-10 is expressed in terms of pg/ml.

Measurement of Th1/Th2 cell ratio

The Th1/Th2 cell ratio was assayed by a conventional method using Helper T (Th) cell line three color analysis test. Th1/Th2 cell ratio (or simply Th1/Th2 ratio) means the ratio of cells producing IFN-γ (Th1) to cells producing IL-4 (Th2) among Helper T cells having cell surface antigen CD4 and expressed as CD4×IFN-γ/IL-4.

First, the blood of a patient suffering a cancer was treated with phorbol 12-Myristate 13 Acetate and Ionomycin at 37° C. for 4 hours to stimulate the cells in the blood to produce cytokines. Then, Breferdin A was added to terminate the production reaction. Using CD4-PC5 (Beckman Coulter), i.e., an anti-CD4 antibody, a cell surface marker CD4 was stained. After fixing, the cells were subjected to haemolysis treatment using FACS Lysing Solution (Japan Becton Dickinson). Thereafter, cell membrane permeation treatment was performed using FACS Permeabilizing Solution (Japan Becton Dickinson). Further, the cytokines in the cells were stained with anti-IFN-γ antibody/anti-IL-4 antibody (FAST IMMUNE IFN-γ FITC/IL-4 PE, Japan Becton Dickinson) and measurement and analysis was made using a low cytometer (FACS Calibur, Becton Dickinson).

Based on the above measurement data, the correlation among cytokines were analyzed.

FIG. 1 is a general diagram illustrating the correlation among cytokines. FIG. 1 revealed that there are strong positive correlation between Th1/Th2 ratio and IL-12, Th1/Th2 ratio and IFN-γ, IFN-γ and IL-12, IL-12 and CD3×CD161 (NKR-P1), IFN-γ and CD3×CD161 (NKR-P1), and there are strong inverse correlation between IL-2 and Vα24Vβ11 (TCR Vα24+/TCR Vβ11+), thus indicating the relationship between each antigen receptor and cytokine.

FIG. 2 illustrates the correlation between the amount of IFN-γ and CD3×CD161 and between that amount and Vα24Vβ11. It revealed that the former (FIG. 2A) shows existence of a strong positive correlation while the latter (FIG. 2B) shows a weak inverse correlation. This suggests that the stimulation to the NKR-P1 have a strong positive correlation with the induction of INF-γ.

FIG. 3 illustrates the correlation between IL-12 (pg/ml) and CD3×CD161. It revealed that the stimulation to the NKR-P1 has a strong positive correlation with the induction of IL-12.

FIG. 4 illustrates the correlation between IL-12 and Vα24Vβ11. It revealed that the stimulation to the Vα24Vβ11 has a strong inverse correlation with the induction of IL-12.

Figure 5:
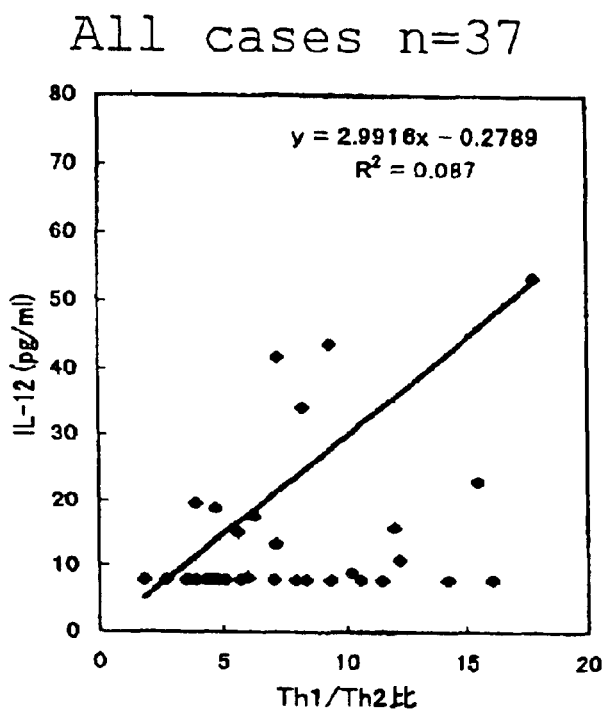
FIG. 5 is a diagram illustrating the correlation of Th1/Th2 ratio with IL-12.

FIG. 5 illustrates the correlation between Th1/Th2 ratio and IL-12, which is a strong positive correlation. This suggests that IL-12 directly act on NKT cells to increase production of INF-γ such that the immune response is directed to the direction where Th1 can act.

Figure 6:
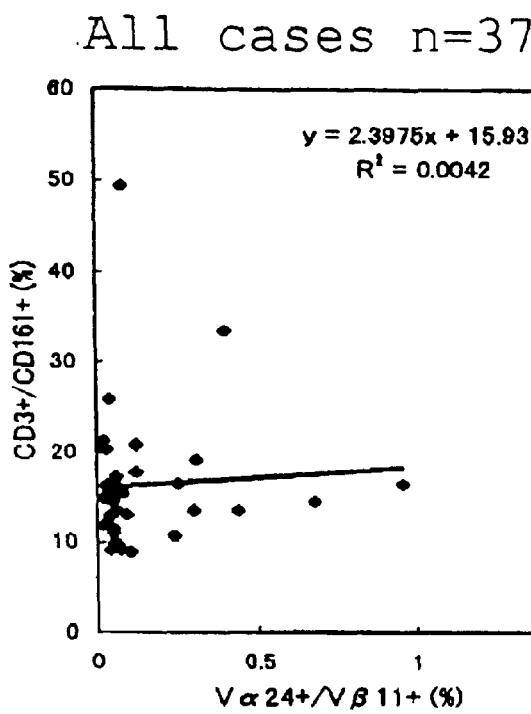
FIG. 6 is a diagram illustrating the correlation of Vα24Vβ11 with CD3×CD161.

FIG. 6 illustrates the correlation between Vα24Vβ11 and CD3×CD161. It revealed that the both have no correlation with each other.

FIG. 7 illustrates the correlation between Vα24Vβ11 and Th1/Th2 ratio. These show a weak inverse correlation with each other.

Figure 8:
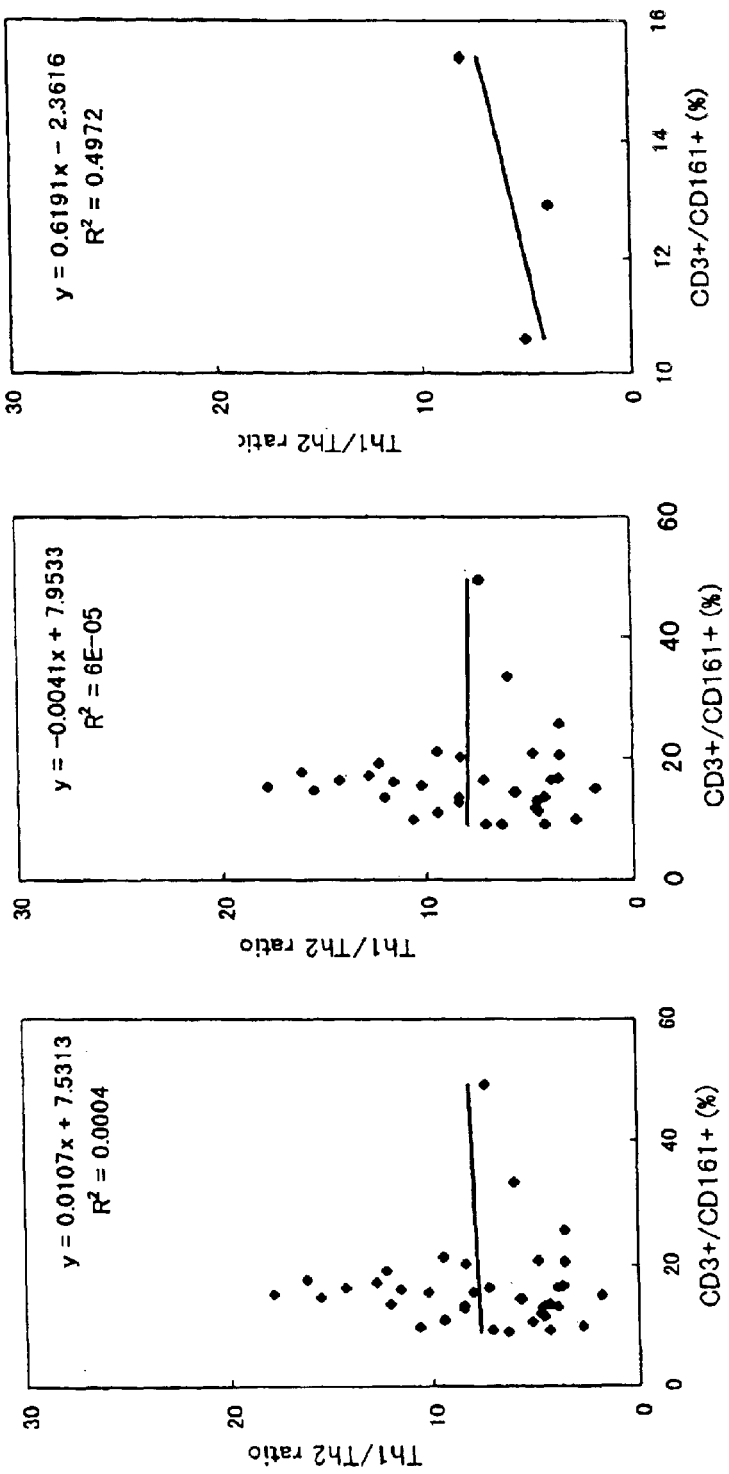
FIG. 8 is a diagram illustrating the correlation of CD3×CD161 with Th1/Th2 ratio.

FIG. 8 illustrates the correlation between CD3×CD161 and Th1/Th2 ratio. These show a weak positive correlation with each other.

As stated above, it has been demonstrated that NKT cells of which T cell antigen receptor for Vα24Vβ11 are stimulated show strong inverse correlation with IL-12 and also show weak correlation with IFN-γ and Th1/Th2. This reveals that the stimulation to Vα24Vβ11 serves to suppress the immunological function. On the other hand, when NKR-P1 of NKT cells is stimulated, the stimulation has strong positive correlation with the induction of IL-12 and IFN-γ and weak correlation with Th1/Th2 ratio. Thus it revealed that the stimulation to the NKR-P1 serves to activate the immunological function.

Advantageous Effects of the Invention

In the present invention, the present inventor has studied the cancer immunity cascade mechanism in the prevention or therapy of cancers and has found that in the cascade in which activated NKT cells that bear cancer immunity are involved, the antigen receptors of NKT cells, NKR-P1 and Vα24Vβ11, have quite different function on NKT cell activation and also found the utility of substances that selectively act on NKR-P1 and Vα24Vβ11, respectively, and thus have achieved revolutionary effects.

What is claimed is:

1. A method for screening therapeutic agents effective against cancer, comprising; administering a potential therapeutic agent in vivo; and determining the ability of the potential therapeutic agent to activate natural killer T cells by assaying natural killer receptor P1 that exists on the cell surface of natural killer T cells.

2. The method of claim 1, wherein said assaying natural killer P1 receptors that exists on the cell surface of natural killer T cells measures CD3 and CD161 cell surface markers.

* * * * *